(12) United States Patent
Leftin et al.

(10) Patent No.: US 11,464,448 B2
(45) Date of Patent: Oct. 11, 2022

(54) INNATE METABOLIC IMAGING OF CELLULAR SYSTEMS (71) Applicant: Memorial Sloan Kettering Cancer Center, New York, NY (US)

(72) Inventors: Avigdor Leftin, New York, NY (US); Jason Koutcher, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 25 days.

(21) Appl. No.: 16/091,602

(22) PCT Filed: Apr. 7, 2017

(86) PCT No.: PCT/US2017/026600
§ 371 (c)(1),
(2) Date: Oct. 5, 2018

(87) PCT Pub. No.: WO2017/177135
PCT Pub. Date: Oct. 12, 2017

(65) Prior Publication Data
US 2019/0083032 A1    Mar. 21, 2019

Related U.S. Application Data

(60) Provisional application No. 62/320,347, filed on Apr. 8, 2016.

(51) Int. Cl.
*A61B 5/00* (2006.01)
*G06T 7/11* (2017.01)
(Continued)

(52) U.S. Cl.
CPC .......... *A61B 5/4848* (2013.01); *A61B 5/0035* (2013.01); *A61B 5/0036* (2018.08);
(Continued)

(58) Field of Classification Search
CPC ......... A61B 5/4848; A61B 8/085; G06T 7/00; G06T 2207/30004
See application file for complete search history.

(56) References Cited

U.S. PATENT DOCUMENTS

| | | | |
|---|---|---|---|
| 8,886,283 B1* | 11/2014 | Chen | A61B 5/055 |
| | | | 382/128 |
| 2002/0177769 A1* | 11/2002 | Orbach | A61B 5/04005 |
| | | | 600/409 |

(Continued)

FOREIGN PATENT DOCUMENTS

WO    WO-2017/177135 A1    10/2017

OTHER PUBLICATIONS

Chen, C-L. et al., A New Nano-sized Iron Oxide Particle with High Sensitivity for Cellular Magnetic Resonance Imaging, Molecular Imaging and Biology, 13:528-839 (2011).
(Continued)

*Primary Examiner* — Wen W Huang
(74) *Attorney, Agent, or Firm* — Hunton Andrews Kurth LLP (57) ABSTRACT

Described herein are systems and methods for image-based (e.g., MRI-based) spatial and temporal mapping of macrophages and other cell types, without the need for image contrast agents. These systems and methods are particularly useful for imaging macrophages because they naturally store metabolites, such as iron. Alternatively, the systems and methods described herein can be used where contrast agents are administered, rather than looking only at endogenous metabolite deposits.

27 Claims, 6 Drawing Sheets

(51) Int. Cl.
*G06T 7/00* (2017.01)
*G16H 30/20* (2018.01)
*A61B 5/055* (2006.01)
*A61B 5/145* (2006.01)
*A61B 6/03* (2006.01)
*A61B 8/08* (2006.01)
*G06T 15/08* (2011.01)

(52) U.S. Cl.
CPC ............ *A61B 5/0071* (2013.01); *A61B 5/055* (2013.01); *A61B 5/14546* (2013.01); *A61B 5/4866* (2013.01); *A61B 5/7264* (2013.01); *A61B 6/032* (2013.01); *A61B 6/037* (2013.01); *A61B 8/085* (2013.01); *G06T 7/0012* (2013.01); *G06T 7/0016* (2013.01); *G06T 7/11* (2017.01); *G16H 30/20* (2018.01); *G06T 15/08* (2013.01); *G06T 2207/10064* (2013.01); *G06T 2207/10081* (2013.01); *G06T 2207/10088* (2013.01); *G06T 2207/10104* (2013.01); *G06T 2207/10108* (2013.01); *G06T 2207/10121* (2013.01); *G06T 2207/10132* (2013.01); *G06T 2207/30024* (2013.01); *G06T 2207/30096* (2013.01); *G06T 2210/41* (2013.01)

(56) References Cited

U.S. PATENT DOCUMENTS

| | | | | |
|---|---|---|---|---|
| 2006/0293581 | A1* | 12/2006 | Plewes | A61B 5/055 600/407 |
| 2008/0125643 | A1* | 5/2008 | Huisman | A61B 5/14546 600/420 |
| 2011/0044524 | A1* | 2/2011 | Wang | G01R 33/54 382/131 |
| 2011/0098558 | A1* | 4/2011 | Weaver | A61B 5/05 600/420 |
| 2013/0344003 | A1* | 12/2013 | Daldrup-Link | A61K 33/26 424/9.36 |
| 2014/0035943 | A1* | 2/2014 | Statham | G06T 11/001 345/593 |
| 2014/0064589 | A1* | 3/2014 | Dale | G06T 7/0016 382/131 |
| 2014/0219535 | A1* | 8/2014 | Chen | G06T 7/0012 382/131 |
| 2015/0161788 | A1* | 6/2015 | Oh | G06T 7/0016 382/131 |
| 2016/0157806 | A1* | 6/2016 | Han | A61B 6/502 378/54 |
| 2016/0271274 | A1* | 9/2016 | Ivkov | A61B 18/04 |
| 2017/0131284 | A1* | 5/2017 | Kobayashi | G01N 33/84 |
| 2017/0146629 | A1* | 5/2017 | Le Bihan | A61B 5/055 |

OTHER PUBLICATIONS

Hauger, O. et al., USPIO-enhanced MR imaging of macrophage infiltration in native and transplanted kidneys: initial results in humans, Molecular Imaging, Eur Radiol.. 17:2898-2907 (2007).
International Search Report, PCT/US2017/026600, 3 pages, dated Jul. 6, 2017.
Saudek, E. et al., Analysis of Human Brain NMR Spectra in Vivo Using Artificial Neural Networks, ICANN 2008, Part II, LNCS 5L64, pp. 517-526 (2008).
Vigneron, D. B. et al., High Resolution 3D MR Spectroscopic Imaging and J-resolved MRS of the Prostate at 3 Tesla, Proc. Intl. Soc. Mag. Reson. Med., 11:386 (2004).
Written Opinion, PTC/US2017/026600, 6 pages, dated Jul. 6, 2017.
Communication pursuant to Article 94(3) EPC dated May 13, 2020 issued for European Patent Application No. 17722539.8.
Communication pursuant to Article 94(3) EPC dated Feb. 2, 2021 issued for European Application No. 17722539.8.

* cited by examiner

INNATE METABOLIC IMAGING OF CELLULAR SYSTEMS

CROSS-REFERENCE TO RELATED APPLICATION

This application claims the benefit of U.S. Application Ser. No. 62/320,347 filed on Apr. 8, 2016, the disclosure of which is hereby incorporated by reference in its entirety.

GOVERNMENT SUPPORT

This invention was made with government support under grant number W81XWH-13-1-0386 awarded by Department of Defense (DOD). The government has certain rights in the invention.

FIELD OF THE INVENTION

This invention relates generally to image processing techniques. In particular embodiments, the invention relates to processing of an MM image for mapping of cell types based on their endogenous iron concentrations.

BACKGROUND

Stromal infiltration of macrophages is implicated in the progression of many types of cancer, including prostate cancer (PCa). Depletion of tumor-associated macrophages (TAMs) inhibits tumor growth and enhances radiation therapy response. An important factor determining macrophage infiltration is tissue iron load because their high innate iron metabolism primes them towards an iron scavenging immune response. Currently, exogenous iron contrast agents are used with MRI (magnetic resonance imaging) to monitor macrophage levels in vivo. However, iron contrast agents can hyperpolarize the iron metabolism of macrophages promoting a pro-tumor phenotype, therefore biasing the measurement of TAM infiltration.

Thus, current ability to non-invasively assess TAM number, and monitor TAM response over the full course of therapeutic regimens using MRI is limited, leaving a critical gap in the understanding of immune response to cancer therapy and how to enhance it further. This is because label-based MRI approaches are hampered by the contrast agent itself due to various factors, such as variable cell uptake and limited lifetime of the cellular label (<1 week).

There is a need for systems and methods for mapping of cell-types based on their endogenous iron concentrations which do not require administration of iron contrast agents.

SUMMARY OF INVENTION

Described herein are systems and methods for image-based spatial and temporal mapping of macrophages and other cell types, without the need for image contrast agents. These systems and methods are particularly useful for imaging macrophages because they naturally store metabolites such as iron. Alternatively, the systems and methods described herein can be used where contrast agents are administered, rather than looking only at endogenous metabolite (e.g., iron) deposits.

In various embodiments, the approach described herein is referred to as FeMRI. The FeMRI technique exploits the high affinity of macrophages for iron(III) to quantitatively monitor TAM infiltration in vivo without contrast agents. In certain embodiments, the FeMRI technique creates an iron (III) map that covers a discrete quantifiable concentration range at a given magnetic field. The sizes of the concentration ranges are magnetic field dependent, and the detected iron concentration ranges can be divided into an arbitrary number of sub-ranges. Corresponding pixels in these ranges are stratified from the FeMRT maps, and the location and size of pixel clusters having corresponding iron concentrations is measured. The technique has been validated with quantitative histology, and used to measure infiltration of TAMs in orthotopic models of prostate cancer during iron (III) chelation therapy, as described herein. The TAM number was found to be higher in larger tumors, but chelation was able to reduce TAMs and achieve impressive reductions in tumor growth. These results demonstrate the ability to monitor macrophages and their immune response to cancer therapy with the non-perturbing MM approach described herein, and modulate tumor growth and TAM infiltration by targeting their innate metabolism of iron.

Macrophage infiltration appears to be correlated with their innate iron(III) metabolism. The TAM number as estimated non-invasively by FeMRT may serve as a predictor of therapeutic efficacy. By using embodiments of the FeMRT quantitative imaging approach described herein, macrophage infiltration can be monitored over a range of physiological and therapeutic conditions, with the goal of exploiting the immune system to improve therapeutic outcomes and monitor this process. Furthermore, TAMs identified and/or monitored/tracked via the methods and systems described herein may serve as predictive biomarkers of therapeutic response, e.g., during cancer therapy. In certain embodiments, the techniques described herein image, map, and/or monitor iron(III) concentration ranges at a given magnetic field that are helpful for macrophage tracking. For example, the techniques described herein cover a discrete quantifiable concentration range at a given magnetic field (e.g., wherein the concentration range is a range equivalent to or within endpoints of about 0 to about 0.3 mg/g iron, e.g., at 7 T).

In certain embodiments, the systems and methods described herein are applicable to other image types. In other embodiments, the systems and methods described herein are applicable to other image types in addition to the quantitative FeMRI approach described above. For example, macrophage infiltration can be identified in other types of functional (e.g., nuclear) imaging modalities. In particular, FeMRI images can be recorded in combination with CT images and/or PET images in a similar fashion to FeMRI images. Accordingly, in certain embodiments, the systems and methods described herein can be applied to analysis of PET/CT images in order to identify regions of FeMRI images that correspond to particular cell types, as is relevant for assessing states of cancer in a subject.

In certain embodiments, the systems and methods described herein are applicable in drug development and personalized medicine, and can be helpful for monitoring response to various treatments.

In one aspect, the invention is directed to a method of mapping one or more cell types in an image, the method comprising: (a) accessing (e.g., obtaining) an image of a subject; (b) generating a parametric map (e.g., a metabolite (e.g., iron(III)) map) (2D or 3D map) from the image; (c) generating a spatial (2D or 3D) map of pixels (or voxels) within one or more discrete metabolite (e.g., iron) concentration ranges using the parametric map in step (b), thereby identifying each of one or more regions of the image with a corresponding metabolite concentration range; and (d) for each of the one or more regions of the image, identifying a particular cell type according to its corresponding metabolite concentration range.

In certain embodiments, the image comprises an MRI image, a computational tomography (CT) image, a positron emission tomography (PET) image, a single-photon emission computed tomography (SPECT) image, an optical image, fluorescence image, an ultrasound image, and/or any combination thereof. In certain embodiments, the image comprises an MM image.

In certain embodiments, the metabolite depicted in the spatial map comprises a member selected from group consisting of iron, glucose, amino acids, nucleotides, vitamins, antioxidants, proteins, and lipids. In certain embodiments, the metabolite depicted in the spatial map comprises iron (e.g., iron(III)).

In certain embodiments, the image comprises an MRI image, and wherein the metabolite depicted in the spatial map comprises iron (e.g., iron(III)).

In certain embodiments, the parametric map is a visual representation of an indirectly measured parameter that is mapped as a function of a directly recorded imaging parameter. In certain embodiments, the indirectly measured parameter is a member selected from the group consisting of a concentration, a perfusion rate, and a diffusion coefficient, and wherein the directly measured imaging parameter is a member selected from the group consisting of a signal contrast level and a signal relaxation time.

In certain embodiments, the one or more cell types comprise macrophages. In certain embodiments, the one or more cell types comprise tumor-associated macrophages (TAMs). In certain embodiments, the one or more cell types comprise cancer cells (e.g., prostate cancer cells, e.g., breast cancer cells, e.g., melanoma cancer cells) (e.g., wherein the cancer cells comprise a member selected from the group consisting of adrenocortical carcinoma cells, astrocytoma cells, basal cell carcinoma cells, carcinoid cells, cardiac cells, cholangiocarcinoma cells, chordoma cells, chronic myeloproliferative neoplasms cells, craniopharyngioma cells, ductal carcinoma in situ, ependymoma cells, intraocular melanoma cells, gastrointestinal carcinoid tumor cells, gastrointestinal stromal tumor (GIST) cells, gestational trophoblastic disease cells, glioma, histiocytosis cells, leukemia cells, merkel cell carcinoma cells, mesothelioma cells, myeloma cells, myelodysplastic syndrome cells, papillomatosis cells, paraganglioma cells, pheochromacytoma cells, pleuropulmonary blastoma cells, retinoblastoma cells, sarcoma cells, and Wilms' tumor cells).

In certain embodiments, step (b) comprises generating the map (2D or 3D map) from the image using a calibration curve. In certain embodiments, step (b) comprises generating the map (2D or 3D map) from the image using a regression analysis (e.g., wherein the metabolite is iron, e.g., of $R_2^*=1/T_2^*$ vs. mg iron(III) $g^{-1}$).

In certain embodiments, the map covers a discrete quantifiable concentration range at a given magnetic field.

In certain embodiments, the parametric map comprises an iron(III) map, and wherein the concentration range is a range equivalent to or within endpoints of about 0 to about 0.3 mg/g iron, e.g., at 7 T. In certain embodiments, the parametric map comprises an iron(III) map, and wherein the concentration range is a range having at least 0.2 or at least 0.3 mg/g iron as an upper bound. In certain embodiments, the parametric map is an iron(III) map, and wherein the concentration range spans a range at least about 0.1 mg/g iron, e.g., at least about 0.15 mg/g iron, e.g., at least about 0.2 mg/g iron).

In certain embodiments, the given magnetic field affects the discrete quantifiable concentration range, e.g., the specific concentration range (e.g., specific iron concentration range) that is utilized is field strength dependent and varies with magnetic field).

In certain embodiments, the metabolite (e.g., iron) being mapped is endogenous metabolite (e.g., iron) only (i.e., where no metabolite-containing contrast agent has been administered to the subject).

In certain embodiments, the step of generating the spatial (2D or 3D) map of pixels (or voxels) within one or more discrete metabolite concentration ranges using the map in step (b) is conducted by performing histogram-based thresholding of the map.

In certain embodiments, the method comprises quantifying extent of infiltration of tumor-associated macrophages (TAMs) by mapping regions of the image (e.g., MRI image) with high metabolite (e.g., iron) concentration as a function of percent infiltration of a tumor.

In certain embodiments, the metabolite comprises iron, and the high iron concentration is in a range from about 0.1 to about 0.2 mg/g iron (e.g., from 0.15 to 0.16 mg/g iron).

In certain embodiments, the map covers multiple discrete quantifiable ranges, e.g., two or more ranges, e.g., a high range and a low range (e.g., wherein the range is defined by the median of the range at a given magnetic field strength).

In certain embodiments, the metabolite (e.g., iron) concentration is quantified by performing concentric rake sampling.

In certain embodiments, the method further comprises: (e) performing steps (a) to (d) for each of a plurality of images obtained from the subject at different times to monitor progression of macrophages in the subject.

In certain embodiments, the method comprises monitoring immune response to cancer therapy.

In another aspect, the invention is directed to a system for mapping one or more cell types in an image, the system comprising: a processor; and a memory having instructions stored thereon, wherein the instructions, when executed by the processor, cause the processor to: (a) access an image of a subject; (b) generate a parametric map (e.g., a metabolite (e.g., iron(III)) map) (2D or 3D map) from the image; (c) generate a spatial (2D or 3D) map of pixels (or voxels) within one or more discrete metabolite concentration ranges using the map in step (b), thereby identifying each of one or more regions of the image with a corresponding metabolic concentration range; and (d) for each of the one or more regions of the MRI image, identify a particular cell type according to its corresponding metabolite concentration range.

In certain embodiments, the image comprises an MRI image, a computational tomography (CT) image, a positron emission tomography (PET) image, a single-photon emission computed tomography (SPECT) image, an optical image, fluorescence image, an ultrasound image, and/or any combination thereof. In certain embodiments, the image comprises an MM image.

In certain embodiments, the metabolite depicted in the spatial map comprises a member selected from group consisting of iron, glucose, amino acids, nucleotides, vitamins, antioxidants, proteins, and lipids. In certain embodiments, the metabolite depicted in the spatial map comprises iron (e.g., iron(III)).

In certain embodiments, the image comprises an MM image, and wherein the metabolite depicted in the spatial map comprises iron (e.g., iron(III)).

In certain embodiments, the parametric map is a visual representation of an indirectly measured parameter that is mapped as a function of a directly recorded imaging parameter. In certain embodiments, the indirectly measured parameter is a member selected from the group consisting of a concentration, a perfusion rate, and a diffusion coefficient, and wherein the directly measured imaging parameter is a member selected from the group consisting of a signal contrast level and a signal relaxation time.

In certain embodiments, the one or more cell types comprise macrophages. In certain embodiments, the one or more cell types comprise tumor-associated macrophages (TAMs). In certain embodiments, the one or more cell types comprise cancer cells (e.g., prostate cancer cells, e.g., breast cancer cells, e.g., melanoma cancer cells) (e.g., wherein the cancer cells comprise a member selected from the group consisting of adrenocortical carcinoma cells, astrocytoma cells, basal cell carcinoma cells, carcinoid cells, cardiac cells, cholangiocarcinoma cells, chordoma cells, chronic myeloproliferative neoplasms cells, craniopharyngioma cells, ductal carcinoma in situ, ependymoma cells, intraocular melanoma cells, gastrointestinal carcinoid tumor cells, gastrointestinal stromal tumor (GIST) cells, gestational trophoblastic disease cells, glioma, histiocytosis cells, leukemia cells, merkel cell carcinoma cells, mesothelioma cells, myeloma cells, myelodysplastic syndrome cells, papillomatosis cells, paraganglioma cells, pheochromacytoma cells, pleuropulmonary blastoma cells, retinoblastoma cells, sarcoma cells, and Wilms' tumor cells).

In certain embodiments, step (b) comprises generating the map (2D or 3D map) from the image using a calibration curve. In certain embodiments, step (b) comprises generating the map (2D or 3D map) from the image (e.g., Mill) using a regression analysis (e.g., wherein the metabolite is iron, e.g., of $R_2^*=1/T_2^*$ vs. mg iron(III) $g^{-1}$).

In certain embodiments, the map covers a discrete quantifiable concentration range at a given magnetic field.

In certain embodiments, the map comprises an iron(III) map, and wherein the concentration range is a range equivalent to or within endpoints of about 0 to about 0.3 mg/g iron, e.g., at 7 T. In certain embodiments, the parametric map comprises an iron(III) map, and wherein the concentration range is a range having at least 0.2 or at least 0.3 mg/g iron as an upper bound. In certain embodiments, the parametric map comprises an iron(III) map, and wherein the concentration range spans a range at least about 0.1 mg/g iron, e.g., at least about 0.15 mg/g iron, e.g., at least about 0.2 mg/g iron.

In certain embodiments, the given magnetic field affects the discrete quantifiable concentration range, e.g., the specific concentration range (e.g., specific iron concentration range) that is utilized is field strength dependent and varies with magnetic field).

In certain embodiments, the metabolite (e.g., iron) being mapped is endogenous metabolite only (i.e., where no metabolite-containing contrast agent has been administered to the subject).

In certain embodiments, the step of generating the spatial (2D or 3D) map of pixels (or voxels) within one or more discrete metabolite concentration ranges using the map in step (b) is conducted by performing histogram-based thresholding of the map.

In certain embodiments, the instructions cause the processor to quantify extent of infiltration of tumor-associated macrophages (TAMs) by mapping regions of the image (e.g., MRI image) with high metabolite (e.g., iron) concentration as a function of percent infiltration of a tumor.

In certain embodiments, the metabolite comprises iron, and wherein the high metabolite concentration is in a range from about 0.1 to about 0.2 mg/g iron (e.g., from 0.15 to 0.16 mg/g iron).

In certain embodiments, the map covers multiple discrete quantifiable ranges, e.g., two or more ranges, e.g., a high range and a low range (e.g., wherein the range is defined by the median of the range at a given magnetic field strength).

In certain embodiments, the metabolite (e.g., iron) concentration is quantified by performing concentric rake sampling.

In certain embodiments, the instructions cause the processor to: (e) perform steps (a) to (d) for each of a plurality of images (e.g., MM) obtained from the subject at different times to monitor progression of macrophages in the subject.

In certain embodiments, the system monitors immune response to cancer therapy.

Elements of embodiments involving one aspect of the invention (e.g., methods) can be applied in embodiments involving other aspects of the invention (e.g., systems), and vice versa.

DEFINITIONS

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance (e.g., an iron-containing contrast agent) into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

"Cancer": As used herein, the term "cancer" refers to a disease, disorder, or condition in which cells exhibit relatively abnormal, uncontrolled, and/or autonomous growth, so that they display an abnormally elevated proliferation rate and/or aberrant growth phenotype characterized by a significant loss of control of cell proliferation. In certain embodiments, a cancer may be characterized by one or more tumors. Those skilled in the art are aware of a variety of types of cancer including, for example, adrenocortical carcinoma, astrocytoma, basal cell carcinoma, carcinoid, cardiac, cholangiocarcinoma, chordoma, chronic myeloproliferative neoplasms, craniopharyngioma, ductal carcinoma in situ, ependymoma, intraocular melanoma, gastrointestinal carcinoid tumor, gastrointestinal stromal tumor (GIST), gestational trophoblastic disease, glioma, histiocytosis, leukemia (e.g., acute lymphoblastic leukemia (ALL), acute myeloid leukemia (AML), chronic lymphocytic leukemia (CLL), chronic myelogenous leukemia (CML), hairy cell leukemia, myelogenous leukemia, myeloid leukemia), lymphoma (e.g., Burkitt lymphoma [non-Hodgkin lymphoma], cutaneous T-cell lymphoma, Hodgkin lymphoma, mycosis fungoides, Sezary syndrome, AIDS-related lymphoma, follicular lymphoma, diffuse large B-cell lymphoma), melanoma, merkel cell carcinoma, mesothelioma, myeloma (e.g., multiple myeloma), myelodysplastic syndrome, papillomatosis, paraganglioma, pheochromacytoma, pleuropulmonary blastoma, retinoblastoma, sarcoma (e.g., Ewing sarcoma, Kaposi sarcoma, osteosarcoma, rhabdomyosarcoma, uterine sarcoma, vascular sarcoma), Wilms' tumor, and/or cancer of the adrenal cortex, anus, appendix, bile duct, bladder, bone, brain, breast, bronchus, central nervous system, cervix, colon, endometrium, esophagus, eye, fallopian tube, gall bladder, gastrointestinal tract, germ cell, head and neck, heart, intestine, kidney (e.g., Wilms' tumor), larynx, liver, lung (e.g., non-small cell lung cancer, small cell lung cancer), mouth, nasal cavity, oral cavity, ovary, pancreas, rectum, skin, stomach, testes, throat, thyroid, penis, pharynx, peritoneum, pituitary, prostate, rectum, salivary gland, ureter, urethra, uterus, vagina, or vulva.

"Cells": As used herein, the term "cells" includes any normal or diseased cells including, but not limited to, cells such as trichocytes, keratinocytes, gondaotrophes, corticotropes, thyrotropes, somatorropes, lacroptrophs, neurons, glia cells, chromaffin cells, parafollicular cells, glomus cells, melanocytes, Merkel cells, odontoblasts, cementoblasts, keratocytes, ependymocytes, pinealocytes, enteroendocrines, S cells, delta cells, goblet cells, Paneth cells, tuft cells, enterocytes, hepatocytes, hepatic stellates, Kuppfer cells, cholestocytes, centroacinar cells, pancreatic stellate cells, alpha cells, beta cells, F cells, thyroid cells, parathyroid cells, urothelial cells, osteoblasts, osteolytes, chrodblasts, chondrocytes, lipoblasts, adipocytes, myoblasts, mycocytes, myosatellaites, tendon cells, cardiac cells, fibroblast cells, fibrocytes, interstitial cells of Cajal, angioblasts, endothelial cells, mesangial cells, juxtaglomerular cells, macula densa cells, stroma cells, telocytes, simple epithelial cells, podocytes, kidney proximal tubule brush border cells, sertoli cells, leydig cells, granulosa cells, peg cells, germ cells, lymphoid cells, myeloid cells, endothelial progenitor cells, endothelial colony forming cells, endothelial stem cells, angioblasts, pericytes, and mural cells.

"Detector": As used herein, the term "detector" includes any detector of electromagnetic radiation used during the acquisition of an image using techniques such as, but not limited to, X-ray radiography, magnetic resonance imaging, ultrasonography, endoscopy, elastography, tactile imaging, thermography, photography, nuclear, positron emission tomography, and single-photon emission computed tomography.

"Disease": As used herein, the term "disease" refers to any abnormal medical condition caused by factors including, but not limited to, cancer, cutaneous conditions, endocrine disorder, infection, acquired disorders congenital, genetic, hereditary, Iatrogenic disorder, idiopathic disorders, liver disorders, heart disorders, and metabolic disorders.

"Image": The term "image", as used herein, includes any visual representation, such as a photo, a video frame, streaming video, as well as any electronic, digital or mathematical analogue of a photo, video frame, or streaming video. An image can be two-dimensional or three-dimensional. A three-dimensional image may be stored and/or rendered as a dataset in three dimensions and/or may be displayed as a set of two-dimensional representations, or as a three-dimensional representation. Systems described herein, in certain embodiments, includes a display for displaying an image or any other result produced by the processor. Methods described herein, in certain embodiments, include a step of displaying an image or any other result produced via the method. For example, an image comprises a magnetic resonance image, a computational tomography (CT) image, a positron emission tomography (PET) image, an optical image, a fluorescence image, an ultrasound image, or any combination thereof.

"Metabolite": The term "metabolite", as used herein, includes any exogenous or endogenous chemical substance, or chemical reaction products from these substances. Metabolites can be, but are not limited to, iron, glucose, amino acids, nucleotides, vitamins, antioxidants, proteins, and lipids.

"Parametric map": The term "parametric map", as used herein, is a visual representation of an indirectly measured parameter that is mapped as a function of a directly recorded imaging parameter using a theoretical or empirical mathematical relationship between the variables. A directly recorded imaging parameter may include, but is not limited to, a signal contrast level or a signal relaxation time, while an indirectly recorded imaging parameter may include, but is not limited to, a concentration, perfusion rate, or diffusion coefficient, for example. The mathematical relationship allowing the directly measured parameter to be expressed in terms of the indirectly measured parameter may include, but is not limited to, linear regression, non-linear regression, or other statistical analysis.

"Subject": As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relieves, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition. In certain embodiments, treatment comprises delivery of therapeutics, including but not limited to, small molecule delivery, radiotherapy, immunotherapy, intrinsic therapeutic properties (e.g., ferroptosis), and particle-driven regulation of the tumor microenvironment. In certain embodiments, therapeutics are attached to particles, such as those described herein.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIGS. 1A-1E show that FeMRI is a label-free probe of endogenous iron(III). These data demonstrate the ability to map iron(III) in vitro and in vivo.

FIGS. 2A-2J show that FeMRI mapping of iron(III) enables TAM infiltration to be quantified in prostate cancer models. This data demonstrates identification of TAM clusters using FeMRI, and provides a validation of these MRI measurements with quantitative histology.

FIGS. 3A-3D show that tumor growth and TAM infiltration are reduced during iron chelation therapy. This data demonstrates the ability to monitor tumor growth and TAMs using FeMRI and histology in two orthotopic prostate cancer models over the full course of therapy.

DESCRIPTION

Throughout the description, where systems are described as having, including, or comprising specific components, or where methods are described as having, including, or comprising specific steps, it is contemplated that, additionally, there are systems of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Various embodiments described herein have applicability in the diagnosis, evaluation, staging, and/or treatment of cancer, inflammation, heart disease, thalassemia, hereditary and transfusion-dependent iron-overload disorder, anemia, kidney/endocrine disorder, myeloproliferative disorder, neurodegeneration, stroke, diabetes, metabolic disorder, and/or immune disorder.

The status quo of current macrophage infiltration measurements relies on invasive histological sampling. The translational potential of MRI measurements of TAMS is hindered by the need for exogenous iron contrast agents. In order to overcome this bottleneck, methods and systems described herein present a label-free MRI approach that can measure macrophage infiltration during the diagnosis, evaluation, staging, and/or treatment of disease in vivo. Data presented herein suggest that the FeMRI method in orthotopic syngeneic models can be used to monitor TAM infiltration during growth and iron chelation. These findings represent a substantive departure from the status quo by not only correlating TAM infiltration with therapeutic response using a non-perturbing MRI technique, but also by identifying a putatively direct role of iron metabolism in TAM infiltration and tumor growth. FeMRI and molecular cytology can be used to investigate the effects of (1) iron and (2) radiation and immune therapy on macrophage infiltration and tumor growth. Techniques presented herein allow use of MRI (alone or in combination with other imaging systems and methods) to assess response to radiation and immune therapy at the cellular level. Further, techniques presented herein allow the use of MRI (alone or in combination with other imaging systems and methods) to be applicable in personalized medicine and drug development.

In certain embodiments, the systems and methods described herein are applicable to other image types, in addition to the quantitative FeMRI approach described above. For example, macrophage infiltration can be identified in other types of functional (e.g., nuclear) imaging modalities. In particular, FeMRI images can be recorded in combination with CT images and/or PET images in a similar fashion to FeMRI images. Accordingly, in certain embodiments, the systems and methods described herein can be applied to analysis of PET/CT images in order to identify regions of FeMRI images that correspond to particular cell types, as is relevant for assessing states of cancer in a subject.

EXAMPLES

Experiment A presented below demonstrates monitoring of macrophages endogenously through their high innate metabolism of iron(III). Experiment B presented below demonstrates the feasibility of measuring macrophage depletion in tumors during iron(III) chelation therapy. Thus, it is identified that, in addition to the role of iron(III) on macrophage response, iron(III) also plays a key role in TAM infiltration in prostate cancer. Without wishing to be bound to any particular theory, it is believed that iron accumulation in tumors supports the polarization of TAMs toward a tumorigenic state and increases their infiltration, while iron depletion can reduce tumor growth and TAM infiltration. By monitoring systemic modulation of iron in situ and ex vivo, it is possible to determine the dependence of macrophage immune response on iron, providing new insight into the involvement of iron in macrophage immune response in cancer, leading to new therapeutic strategies and expanding the working range of FeMRI for both preclinical and clinical implementation.

Experiment A: Mapping TAM Infiltration in Prostate Cancer Using a Generalizable Label-Free MRI Approach The quantification of endogenous iron(III) by MRI has been proposed as a replacement for invasive biopsy of the liver or heart. This technique has not heretofore been used to measure iron(III) clinically, or preclinically in cancer. Thus, described below is the use of MM relaxometry as a tool for monitoring cellular iron in orthotopic models of prostate cancer as shown in FIGS. 1A-1E. The $T_2$*-weighted FeMRI signal (FIG. 1A), or more quantitatively, the nuclear spin relaxation rate $R_2$*, follows a linear dependence on the concentration of iron(III) ([iron(III)], FIG. 1B) allowing the generation of parametric [iron(III)] maps with $T_2$* relaxometry, shown for an iron containing phantom (FIG. 1C) and in vivo for orthotopic MycCaP prostate tumor (FIG. 1E) and other tissues such as liver, spleen, skeletal muscle, and brain (data not shown).

Figures 1A, 1B:
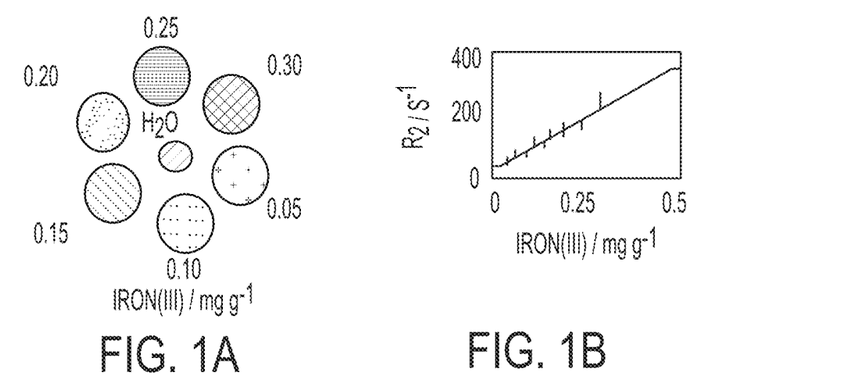
FIGS. 1A and 1B show $T_2^*$-weighted MRI of 0-0.3 mg $Fe(NO_3)_3$ $g^{-1}$ $H_2O$ that was obtained (FIG. 1A) and that $R_2^* = 1/T_2^*$ vs. mg iron(III) $g^{-1}$ was fit with linear trend line (n=3 phantoms, +/−s.e.m.) (FIG. 1B).
Figure 1C:
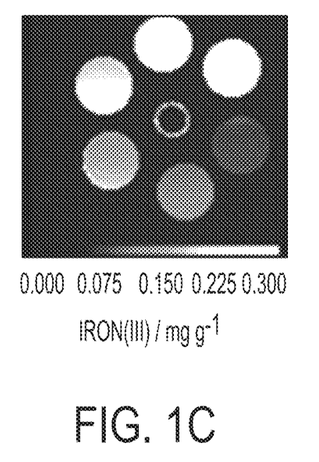
FIG. 1C shows a [iron(III)] parametric map that was generated based on the regression analysis described herein. Dashed circle shows position of $H_2O$ sample and the color bar corresponds to mg iron(III) $g^{-1}$.
Figure 1D:
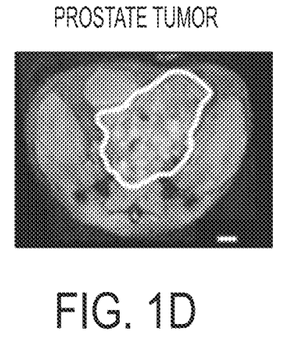
FIG. 1D shows a T2* weighted MRI that was obtained in vivo for mouse torso bearing an orthotopic MycCaP prostate tumor in yellow lines (in-plane pixel resolution≈0.01 μm², 0.5 mm slice thickness).
Figure 1E:
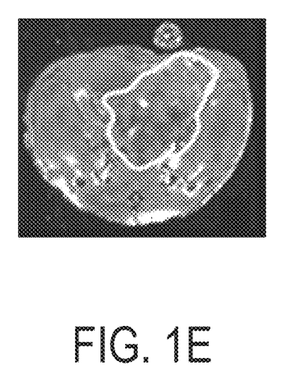
FIG. 1E shows [iron(III)] maps of prostate were then constructed as in FIG. 1C. Scale bar=2 mm.
Figure 2A:
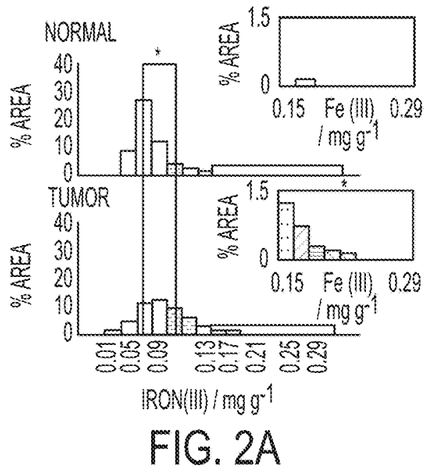
FIGS. 2A-2C show FeMRI [iron(III)] distributions that were constructed from the maps of normal prostate (upper, n=5 mice, +/−s.e.m.) and prostate tumor (lower, n=10, +/−s.e.m.). Boxes show ranges of low- and high-[iron(III)] populations that significantly changed (*p<0.05 1-way ANOVA). Insets are expansions of the high-[iron(III)] range. Thresholded FeMRI [iron(III)] maps were prepared that showed distribution of (FIG. 1B) low-[iron(III)] and (FIG. 1C) high-iron(III) populations (scale bar=2 mm).
Figure 2B:
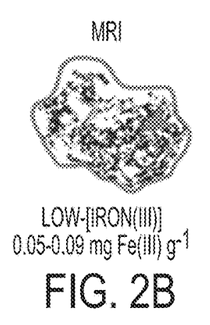
Figure 2C:
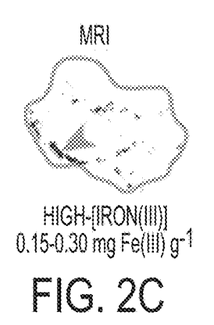

The FeMRI [iron(III)] maps of normal prostate (FIG. 1A, top) and tumor were compared (FIG. 2A, bottom) in order to evaluate differences in their cellular iron distributions. The [iron(III)] mean shifted from approximately 0.05 mg iron(III) g$^{-1}$ in normal tissue to 0.09 mg iron(III) g$^{-1}$ in tumor (n=5 normal, n=10 tumor, *p<0.05), and a high-[iron (III)] sub-population (blue box, 0.15-0.30 mg iron(III) g$^{-1}$) appeared in the tail of the tumor [iron(III)] distribution that was nearly absent in the normal prostate (FIG. 2A, insets, n=5 normal, n=10 tumor, *p<0.05)). These low-[iron(III)] and high-[iron(III)] populations were mapped by thresholding the tumor Fe[(III)] distribution in these ranges on the FeMRI. The low-[iron(III)] map consisted of dense pixel clusters distributed throughout the tumor, while the high-[iron(III)] map contained sparse clusters with average cluster size of approximately 4 MRI pixel$^2$≈0.05 mm$^2$ primarily at the outer tumor margins (n=10 mice).

Figure 2D:
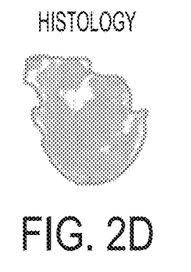
FIGS. 2D-2E shows Prussian Blue iron(III) staining of whole tumor slices, and mapped iron(III) positive regions (scale bar=2 mm). Low-iron(III)⁻ regions and high-iron (III)⁻ populations clusters are indicated by arrows.
Figure 2E:
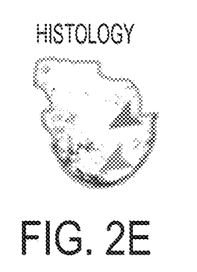
Figure 2F:
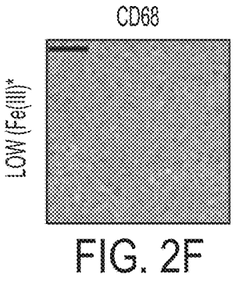
FIGS. 2F-2I show a quantitative analysis of these fields for (FIG. 2F, FIG. 2H) CD68, and (FIG. 2G, FIG. 2I) Prussian Blue iron(III) revealed low-iron(III)⁺ CD68⁻ cancer cells, and high-iron(III)⁺ CD68⁺ TAMs (scale bar=50 μm, field of view 0.05 mm²≈4 MRI pixel², inset 5× expansion of black box).
Figure 2G:
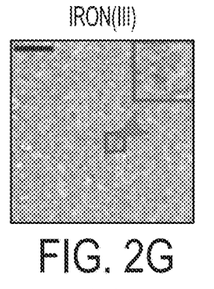
Figure 2H:
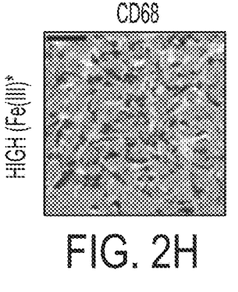
Figure 2I:
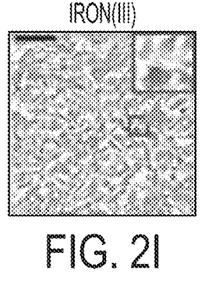

In order to further quantify these low- and high-[iron(III)] sub-populations, quantitative histology was used. Paraffin embedded whole prostate tumor midsections (FIG. 2D, 2E) were stained for iron(III) with Prussian Blue and analyzed (FIG. 2E) to reveal sparse clusters of high-iron(III)$^+$ deposits (FIG. 2E) found primarily at the tumor margins, approximately 0.05 mm$^2$ in size (4 MRI pixels), same as seen by FeMRI (p>0.05). Quantification of CD68 (FIG. 2F, 2H) and Prussian Blue iron(III) (FIG. 2G, 2I) in these clusters, as well as fields of the same size but not containing these large iron(III)$^+$ deposits (low-iron(III)$^+$) revealed two distinct iron (III)$^+$ cell types. In low-iron(III)$^+$ regions, prostate cancer cells were found sparsely studded with ferritin particles less than 1 μm$^2$ (at an approximate density of 1000 ferritin particles/field; no CD68$^+$ macrophages were observed (FIG. 2F, 2G n=18 fields, n=6 mice). In high-iron(III)$^+$ regions CD68$^+$ TAMs were found bearing dense hemosiderin deposits in groups of approximately 24 macrophages/TAM cluster (FIG. 2F, 2G, n=18 fields, n=6 mice). With these histological findings, it was possible to estimate the per-pixel TAM number in high-[iron(III)] MRI clusters at approximately 6 macrophages/pixel.

Figure 2J:
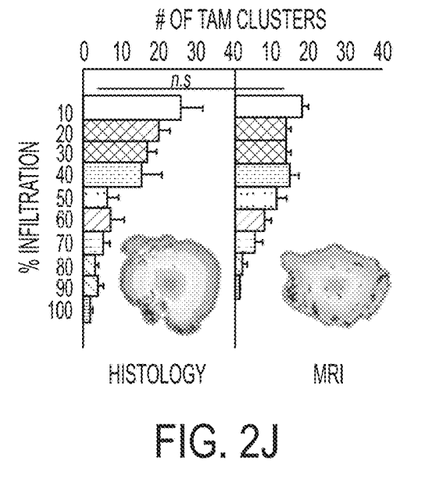
FIG. 2J shows a number of TAM clusters was plotted against percent infiltration into the tumor for (left) high-iron (III)⁺ CD68⁺ clusters in whole slice histology, and (right) high-[iron(III)] clusters for FeMRI (Histology n=6 mice; MM, n=10 mice; +s.e.m.; one way ANOVA, n. s. not significant p<0.05). All data is from orthotopic MycCaP tumors in syngeneic FVB/N mice.

To quantify the extent of infiltration of these TAM clusters, an image-processing algorithm was developed in-house with Matlab and ImageJ. This tool is based on concentric rake sampling that identifies high-iron(III)$^-$ CD68$^+$ or high-[iron(III)] colonies and maps them as a function of % infiltration into the tumor (inset FIG. 2J, 10% outer edge, 100% tumor center) for arbitrarily sized histological (FIG. 2J, left inset) and FeMRI (FIG. 2J, right inset) regions of interest. Analysis of these infiltration profiles revealed that the histological and FeMRI approaches yielded statistically identical maps of TAM infiltration (Histology n=6 mice; MRI, n=10 mice n.s. p>0.05). This further supports that high-[iron(III)] and high-iron(III)$^-$ CD68$^+$ clusters are equivalent TAM populations. This is a demonstration of a simple and highly translatable, label-free MRI approach enabling the mapping of TAM infiltration with an unprecedented in vivo pixel-sensitivity of a few cells.

Experiment B: Monitoring TAM Infiltration during Prostate Cancer Therapy

Preliminary data presented below indicates that FeMRI and histology can be used in combination with iron chelation therapy to monitor reductions in TAM infiltration that coincide with significant inhibition of prostate tumor growth in immune competent orthotopic models. This therapeutic effect resembles macrophage depletion caused by immune therapies such as CSF1R inhibition that also have succeeded in reducing tumor growth, and sensitize tumors to radiation. Thus, FeMRT and histology can be used to monitor TAM infiltration during (1) radiation, (2) CSF1R targeted immune therapy, and (3) iron chelation. Without wishing to be bound to any particular theory, it is believed that depletion of TAMs by immune therapy and chelation will inhibit tumor growth and sensitize tumors to radiation. The biomarker potential of TAM infiltration can lead to improved predictions of therapeutic response using a highly translatable combination of FeMRT and histology. FeMRI can be used as a translational technique that provides cellular-level biomarkers of immune response.

Figure 3A:
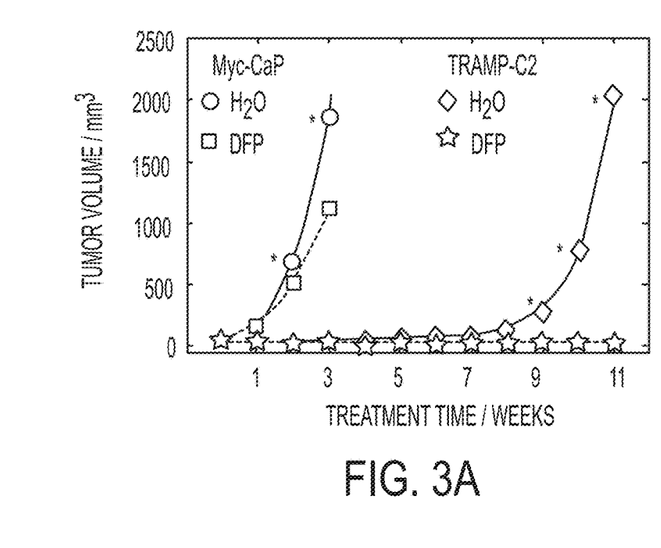
FIG. 3A shows tumor volume that was measured from MM during treatment orthotopic MycCaP and TRAMP-C2 prostate models in syngeneic hosts with the chelator deferiprone (DFP, 150 mg/kg daily by gavage, MycCaP n=10 mice, TRAMP-C2 n=10 mice; +s.e.m.; two-tailed t-test, *p<0.05).
Figure 3B:
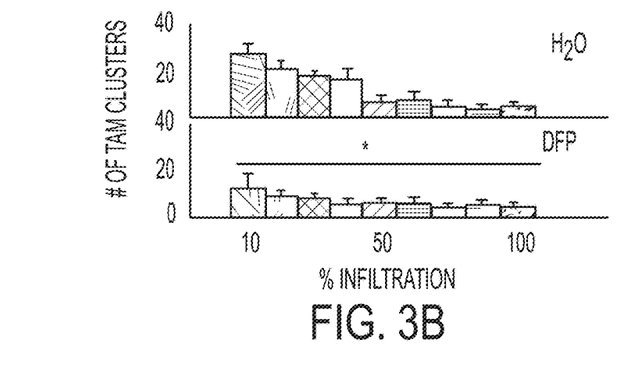
FIG. 3B shows that a number of high-iron(III)⁻ CD68⁺ TAM colonies vs. percent infiltration was quantified from whole slice histology at week 3 of treatment in MycCaP tumors (n=6 mice; +s.e.m.; *p<0.05 1-way ANOVA w.r.t. $H_2O$).
Figure 3C:
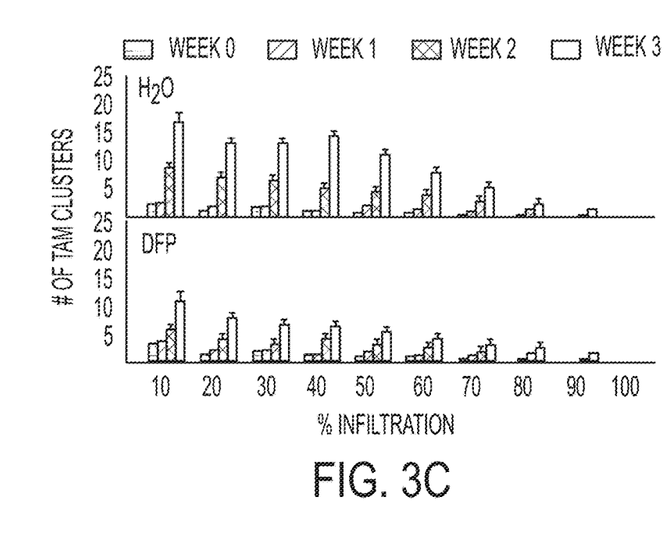
FIG. 3C shows that a number of high-[iron(III)] TAM clusters was measured by FeMRI at each week of treatment as a function of percent infiltration in MycCaP tumors.
Figure 3D:
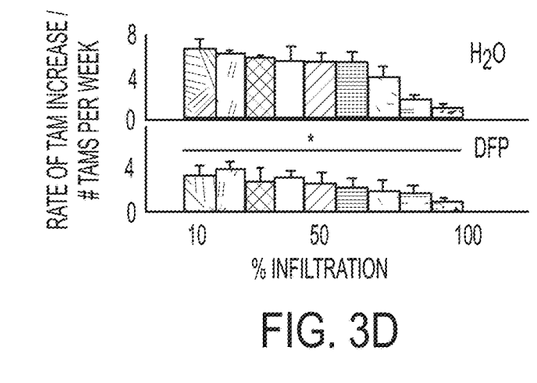
FIG. 3D shows rates of infiltration (vs. percent infiltration was derived from FIG. 3C. (n=10 mice; +s.e.m.; *p<0.05 1-way ANOVA w.r.t. $H_2O$).

Chelation of iron(III) has been proposed as a cancer treatment that causes reductions in tumor growth, presumably by reducing bioavailability of iron(III) to the cancer cells. However, no studies have addressed the possibility that chelation modulates TAM infiltration contributing to these anti-tumor effects. In order to investigate anti-tumor effects of iron chelation, FeMRI is used, as described herein, to monitor tumor growth in two mouse models. The faster growing MycCaP model and the slower growing TRAMP-C2 model were studied and contrasted to evaluate the effect of dose duration. Immune-competent, syngeneic murine FVB/N and C57BL/6 hosts underwent orthotopic prostatic injections of $5 \times 10^4$ cells (MycCaP and TRAMP-C2, respectively), and thereafter received either sham ($H_2O$) or DFP (150 mg/kg, 5 days/week) by oral gavage until average primary tumor burden exceeded 1 $cm^3$ (determined by MM) in the treated group. In the MycCaP model, two weeks of DFP gavage beginning one-week post-implantation at 100 $mm^3$ resulted in 40% smaller tumor volumes by the endpoint of the study (FIG. 3A, n=10, *p<0.05). At long dose durations (12 weeks) there was no growth of TRAMP-C2 orthotopic tumors implanted in syngeneic hosts (FIG. 3A, n=10, *p<0.001). Histological analysis of MycCaP tumors showed reduced high-iron(III)$^+$ and CD68$^+$ positive cells in the DFP treated cohort (data not shown) and the histological TAM infiltration profile of MycCaP tumor at week 3 of treatment showed less TAMs than the untreated group (FIG. 3B, n=10, *p<0.05). FeMRI measurements of TAMs similarly showed reductions with DFP, and allowed the monitoring of TAMs over the full course of treatment (FIG. 3C). The changes of the infiltration profiles over time were analyzed to yield rates of TAM increase during tumor growth. Deferiprone reduced the rates of TAM infiltration that were coincident with reductions of tumor growth. (FIG. 3D, n=10, *p<0.05). Thus, this data supports an "off-label" use for DFP, an approved drug in other diseases; modulation of innate iron metabolism leads to reduction in rates of high-TAM infiltration and causes marked inhibition of tumor growth. Further, the ability to monitor TAM dynamics serially using FeMRI represents a technique that has translational use, bypassing the necessity for using invasive biopsy to obtain similar measures of stromal response to therapy.

Illustrative Network Environment

Figure 4:
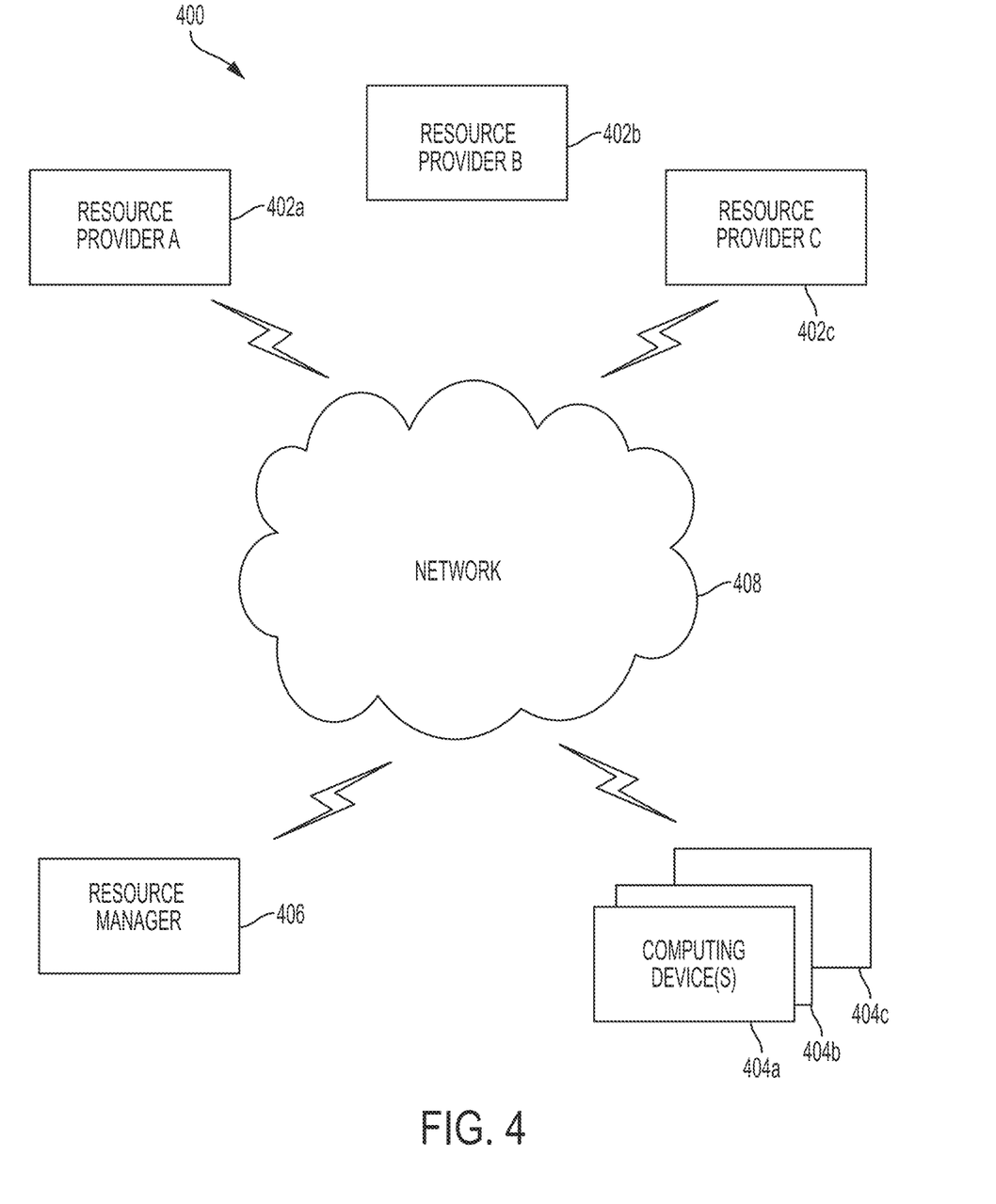
FIG. 4 is an implementation of a network environment 400 for use in providing systems, methods, and architectures for retrieving, managing, and analyzing clinical trial data from a plurality of sources, according to an illustrative embodiment of the invention.

As shown in FIG. 4, an implementation of a network environment 400 for use in providing systems, methods, and architectures for retrieving, managing, and analyzing clinical trial data from a plurality of sources as described herein is shown and described. In brief overview, referring now to FIG. 4, a block diagram of an exemplary cloud computing environment 400 is shown and described. The cloud computing environment 400 may include one or more resource providers 402a, 402b, 402c (collectively, 402). Each resource provider 402 may include computing resources. In some implementations, computing resources may include any hardware and/or software used to process data. For example, computing resources may include hardware and/or software capable of executing algorithms, computer programs, and/or computer applications. In some implementations, exemplary computing resources may include application servers and/or databases with storage and retrieval capabilities. Each resource provider 402 may be connected to any other resource provider 402 in the cloud computing environment 400. In some implementations, the resource providers 402 may be connected over a computer network 408. Each resource provider 402 may be connected to one or more computing device 404a, 404b, 404c (collectively, 404), over the computer network 408.

The cloud computing environment 400 may include a resource manager 406. The resource manager 406 may be connected to the resource providers 402 and the computing devices 404 over the computer network 408. In some implementations, the resource manager 406 may facilitate the provision of computing resources by one or more resource providers 402 to one or more computing devices 404. The resource manager 406 may receive a request for a computing resource from a particular computing device 404. The resource manager 406 may identify one or more resource providers 402 capable of providing the computing resource requested by the computing device 404. The resource manager 406 may select a resource provider 402 to provide the computing resource. The resource manager 406 may facilitate a connection between the resource provider 402 and a particular computing device 404. In some implementations, the resource manager 406 may establish a connection between a particular resource provider 402 and a particular computing device 404. In some implementations, the resource manager 406 may redirect a particular computing device 404 to a particular resource provider 402 with the requested computing resource.

Figure 5:
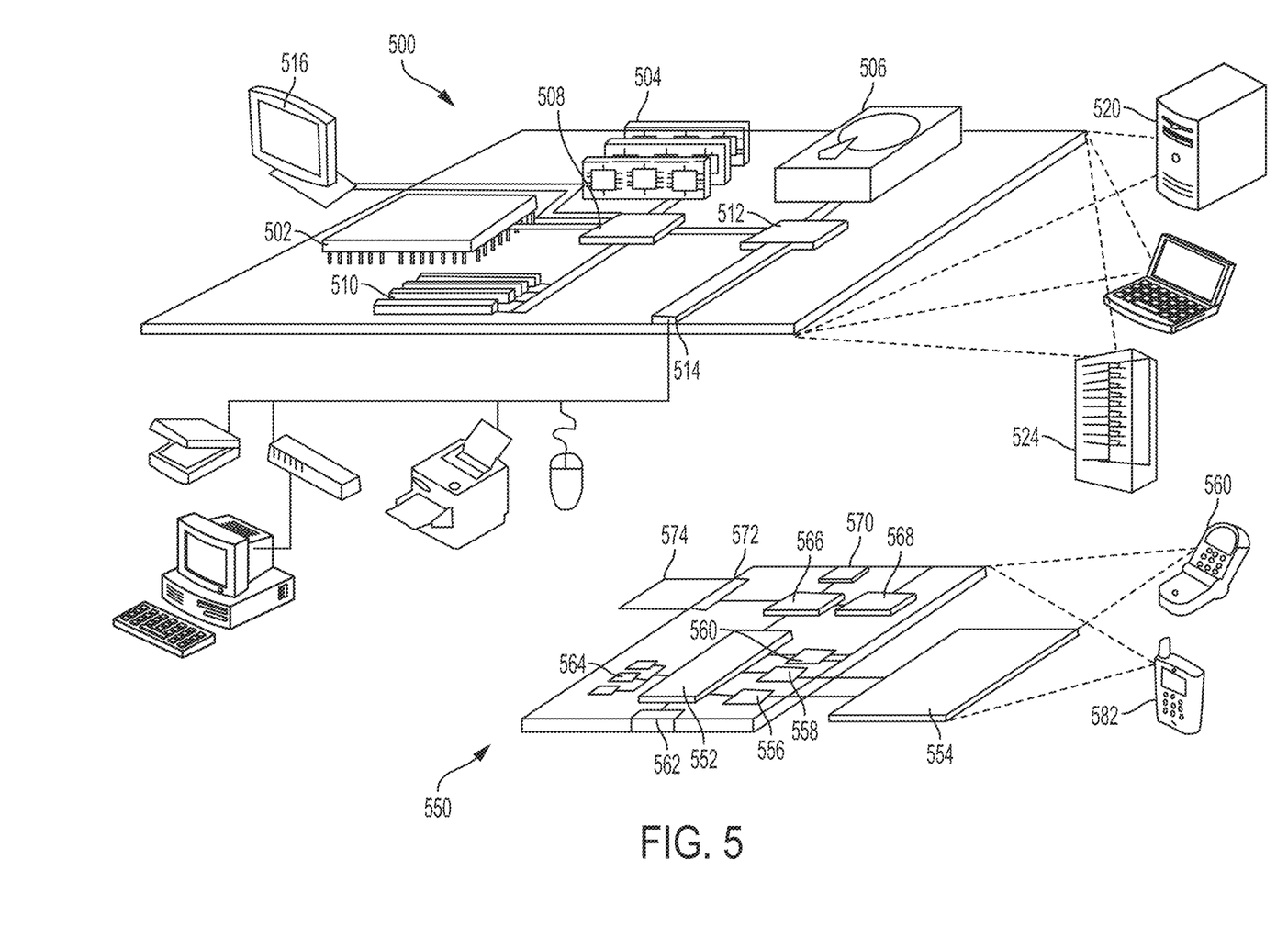
FIG. 5 is an example of a computing device 500 and a mobile computing device 550 that can be used to implement the techniques, for use in illustrative embodiments of the invention.
Figure 6:
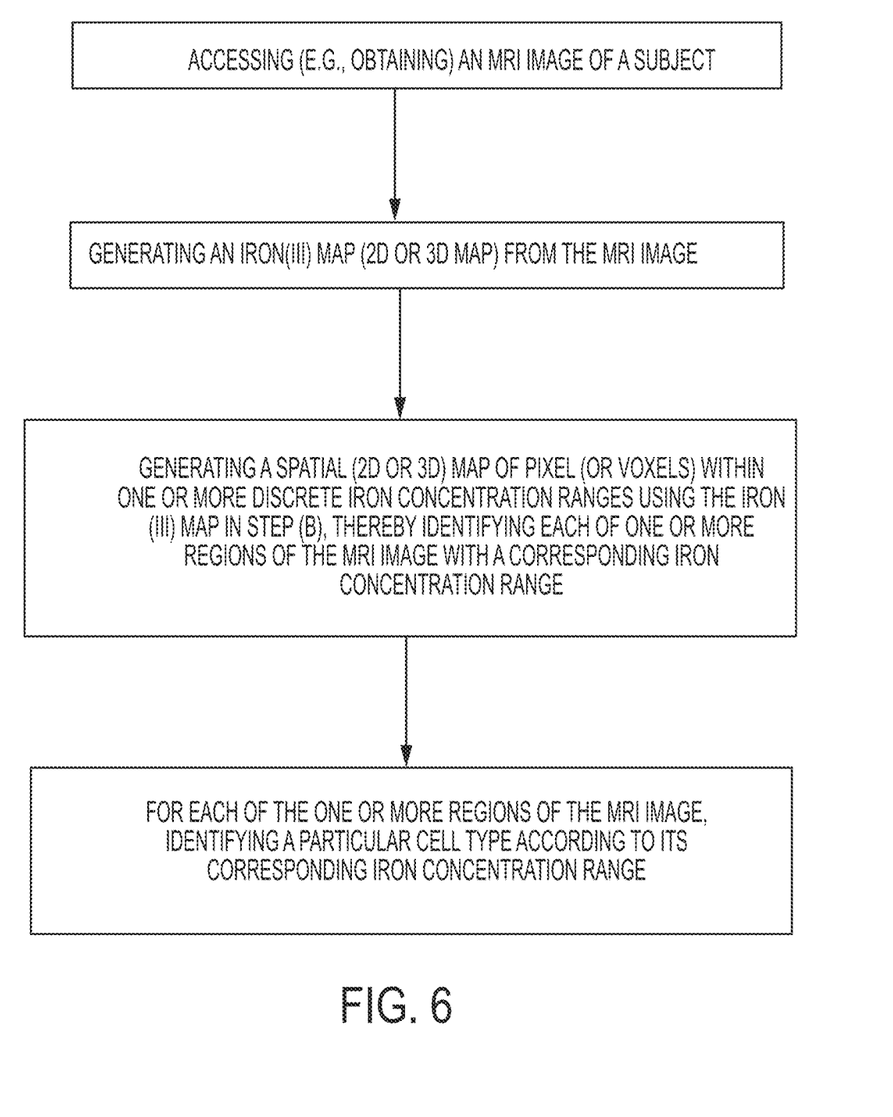
FIG. 6 shows a method of mapping one or more cell types in an MRI image, according to an illustrative embodiment of the invention.

FIG. 5 shows an example of a computing device 500 and a mobile computing device 550 that can be used to implement the techniques described in this disclosure. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a GUI on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system). Thus, as the term is used herein, where a plurality of functions are described as being performed by "a processor", this encompasses embodiments wherein the plurality of functions are performed by any number of processors (one or more) of any number of computing devices (one or more). Furthermore, where a function is described as being performed by "a processor", this encompasses embodiments wherein the function is performed by any number of processors (one or more) of any number of computing devices (one or more) (e.g., in a distributed computing system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth®, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provide as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier. that the instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562.

The mobile computing device 550 may communicate wirelessly through the communication interface 566, which may include digital signal processing circuitry where necessary. The communication interface 566 may provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication may occur, for example, through the transceiver 568 using a radio-frequency. In addition, short-range communication may occur, such as using a Bluetooth®, Wi-Fi™, or other such transceiver (not shown). In addition, a GPS (Global Positioning System) receiver module 570 may provide additional navigation- and location-related wireless data to the mobile computing device 550, which may be used as appropriate by applications running on the mobile computing device 550.

The mobile computing device 550 may also communicate audibly using an audio codec 560, which may receive spoken information from a user and convert it to usable digital information. The audio codec 560 may likewise generate audible sound for a user, such as through a speaker, e.g., in a handset of the mobile computing device 550. Such sound may include sound from voice telephone calls, may include recorded sound (e.g., voice messages, music files, etc.) and may also include sound generated by applications operating on the mobile computing device 550.

The mobile computing device 550 may be implemented in a number of different forms, as shown in the figure. For example, it may be implemented as a cellular telephone 580. It may also be implemented as part of a smart-phone 582, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

In some implementations, the modules described herein can be separated, combined or incorporated into single or combined modules. The modules depicted in the figures are not intended to limit the systems described herein to the software architectures shown therein.

Elements of different implementations described herein may be combined to form other implementations not specifically set forth above. Elements may be left out of the processes, computer programs, databases, etc. described herein without adversely affecting their operation. In addition, the logic flows depicted in the figures do not require the particular order shown, or sequential order, to achieve desirable results. Various separate elements may be combined into one or more individual elements to perform the functions described herein. In view of the structure, functions and apparatus of the systems and methods described here, in some implementations.

Throughout the description, where apparatus and systems are described as having, including, or comprising specific components, or where processes and methods are described as having, including, or comprising specific steps, it is contemplated that, additionally, there are apparatus, and systems of the present invention that consist essentially of, or consist of, the recited components, and that there are processes and methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method of mapping one or more cell types in an image, the method comprising:
   (a) accessing an image of a subject;
   (b) generating at least one of a two-dimensional (2D) parametric map or a three-dimensional (3D) parametric map from the image, wherein the at least one of the 2D parametric map or the 3D parametric map includes a metabolite;
   (c) generating at least one of a spatial 2D map of pixels or a spatial 3D map of voxels within one or more discrete metabolite concentration ranges using the at least one of the 2D parametric map or the 3D parametric map in step (b), thereby identifying each of one or more regions of the image with a corresponding metabolite concentration range; and
   (d) for each of the one or more regions of the image, identifying a particular cell type according to its corresponding metabolite concentration range.

2. The method of claim 1, wherein the image comprises an MM image, a computational tomography (CT) image, a positron emission tomography (PET) image, a single-photon emission computed tomography (SPECT) image, an optical image, fluorescence image, an ultrasound image, and/or any combination thereof.

3. The method of claim 1, wherein the image comprises an MM image.

4. The method of claim 1, wherein the metabolite depicted in the at least one of the 2D spatial map or the 3D spatial map comprises a member selected from group consisting of iron, glucose, amino acids, nucleotides, vitamins, antioxidants, proteins, and lipids.

5. The method of claim 1, wherein the metabolite depicted in the at least one of the 2D spatial map or the 3D spatial map comprises iron.

6. The method of claim 1, wherein the image comprises an MRI image, and wherein the metabolite depicted in the at least one of the 2D spatial map or the 3D spatial map comprises iron.

7. The method of claim 1, wherein the at least one of the 2D parametric map or the 3D parametric map is a visual representation of an indirectly measured parameter that is mapped as a function of a directly recorded imaging parameter.

8. The method of claim 7, wherein the indirectly measured parameter is at least one of a concentration, a perfusion rate, and a diffusion coefficient, and wherein the directly measured imaging parameter is at least one of a signal contrast level or a signal relaxation time.

9. The method of claim 7, wherein the at least one of the 2D parametric map or the 3D parametric map comprises an iron(III) map, and wherein the concentration range is a range equivalent to or within endpoints of about 0 to about 0.3 mg/g iron at 7 T.

10. The method of claim 1, wherein the one or more cell types comprise macrophages.

11. The method of claim 1, wherein the one or more cell types comprise tumor-associated macrophages (TAMs).

12. The method of claim 1, wherein the one or more cell types comprise cancer cells and wherein the cancer cells include at least one of adrenocortical carcinoma cells, astrocytoma cells, basal cell carcinoma cells, carcinoid cells, cardiac cells, cholangiocarcinoma cells, chordoma cells, chronic myeloproliferative neoplasms cells, craniopharyngioma cells, ductal carcinoma in situ, ependymoma cells, intraocular melanoma cells, gastrointestinal carcinoid tumor cells, gastrointestinal stromal tumor (GIST) cells, gestational trophoblastic disease cells, glioma, histiocytosis cells, leukemia cells, merkel cell carcinoma cells, mesothelioma cells, myeloma cells, myelodysplastic syndrome cells, papillomatosis cells, paraganglioma cells, pheochromacytoma cells, pleuropulmonary blastoma cells, retinoblastoma cells, sarcoma cells, or Wilms' tumor cells.

13. The method of claim 1, wherein step (b) comprises generating the at least one of the 2D parametric map or the 3D parametric map from the image using a calibration curve.

14. The method of claim 1, wherein step (b) comprises generating the at least one of the 2D parametric map or the 3D parametric map from the image using a regression analysis, and wherein the metabolite is iron $R_2^* = 1/T_2^*$ vs. mg iron(III) $g^{-1}$.

15. The method of claim 1, wherein the at least one of the 2D parametric map or the 3D parametric map covers a discrete quantifiable concentration range at a given magnetic field.

16. The method of claim 15, wherein the at least one of the 2D parametric map or the 3D parametric map comprises an iron(III) map, and wherein the concentration range is a range having at least 0.2 or at least 0.3 mg/g iron as an upper bound.

17. The method of claim 15, wherein the at least one of the 2D parametric map or the 3D parametric map is an iron(III) map, and wherein the concentration range spans a range at least about 0.1 mg/g iron, at least about 0.15 mg/g iron, or at least about 0.2 mg/g iron.

18. The method of claim 15, wherein the given magnetic field affects the discrete quantifiable concentration range, and wherein the specific iron concentration range that is utilized is field strength dependent and varies with magnetic field.

19. The method of claim 15, wherein the at least one of the 2D parametric map or the 3D parametric map covers multiple discrete quantifiable ranges including a high range and a low range, and wherein the range is defined by the median of the range at a given magnetic field strength.

20. The method of claim 1, where the metabolite being mapped is an endogenous metabolite and wherein no metabolite-containing contrast agent has been administered to the subject.

21. The method of claim 1, wherein the step of generating the at least one of the 2D spatial map or the 3D spatial map within one or more discrete metabolite concentration ranges using the at least one of the 2D parametric map or the 3D parametric map in step (b) is conducted by performing histogram-based thresholding of the at least one of the 2D parametric map or the 3D parametric map.

22. The method of claim 1, further comprising quantifying an extent of infiltration of tumor-associated macrophages (TAMs) by mapping regions of the image with high metabolite concentration as a function of percent infiltration of a tumor.

23. The method of claim 22, wherein the metabolite comprises iron, and the high iron concentration is in a range from about 0.1 to about 0.2 mg/g iron or from about 0.15 to about 0.16 mg/g iron.

24. The method of claim 23, wherein the metabolite concentration is quantified by performing concentric rake sampling.

25. The method of claim 1, further comprising:
(e) performing steps (a) to (d) for each of a plurality of images obtained from the subject at different times to monitor progression of macrophages in the subject.

26. The method of claim 25, comprising monitoring immune response to cancer therapy.

27. A system for mapping one or more cell types in an image, the system comprising:
   a processor; and
   a memory having instructions stored thereon, wherein the instructions, when executed by the processor, cause the processor to:
   (a) access an image of a subject;
   (b) generate at least one of a two-dimensional (2D) parametric map or a three-dimensional (3D) parametric map from the image, wherein the at least one of the 2D parametric map or the 3D parametric map includes from the image;
   (c) generate at least one of a spatial 2D map of pixels or a spatial 3D map of voxels within one or more discrete metabolite concentration ranges using the map in step (b), thereby identifying each of one or more regions of the image with a corresponding metabolic concentration range; and
   (d) for each of the one or more regions of the MM image, identify a particular cell type according to its corresponding metabolite concentration range.

\* \* \* \* \*